(12) United States Patent
Schiller et al.

(10) Patent No.: US 6,786,917 B1
(45) Date of Patent: Sep. 7, 2004

(54) METHOD AND DEVICE FOR PRODUCING A HELPER SIGNAL

(76) Inventors: Alfred Schiller, Steinenstückiweg, 8914 Aeugst a.A. (CH); Günter Stemple, Thorstrasse 13, 86916 Kaufering (DE)

( * ) Notice: Subject to any disclaimer, the term of this patent is extended or adjusted under 35 U.S.C. 154(b) by 0 days.

(21) Appl. No.: 09/255,275

(22) Filed: Feb. 23, 1999

(30) Foreign Application Priority Data

Feb. 26, 1998 (EP) .............................................. 98810156
Jun. 10, 1998 (EP) .............................................. 98110668

(51) Int. Cl.$^7$ ............................................. A61B 5/026
(52) U.S. Cl. ................................................... 607/465
(58) Field of Search ......................... 600/17, 455, 457, 600/465, 513, 439; 607/6

(56) References Cited

U.S. PATENT DOCUMENTS

| | | | |
|---|---|---|---|
| 4,109,642 A | * 8/1978 | Reid et al. .................. | 600/457 |
| 4,582,066 A | 4/1986 | Barnes et al. | |
| 5,156,154 A | * 10/1992 | Valenta, Jr. et al. ......... | 600/455 |
| 5,305,758 A | * 4/1994 | Dietz et al. .................. | 600/455 |
| 5,664,571 A | * 9/1997 | Yamazaki .................... | 600/455 |
| 5,891,036 A | * 4/1999 | Izumi ........................... | 600/455 |

FOREIGN PATENT DOCUMENTS

| | | |
|---|---|---|
| EP | 0 139 285 | 5/1985 |
| EP | 0 421 465 | 4/1991 |
| EP | 0465241 | 1/1992 |
| FR | 2591884 | 6/1987 |
| WO | 91/16000 | 10/1991 |
| WO | 91 16000 | 10/1991 |
| WO | 96/14014 | 5/1996 |

OTHER PUBLICATIONS

Paulo Celso Budri Freire et al. "Computarized Blood–Flow Evaluation in vascular Surgeries with CW Doppler" Cardiology and Imaging, New Orleans, No. 4–7, 1988, Bd. 1, Nr. Conf. 10, Nov. 4, 1988, Harris G.; Walker C.
International Search Report.

* cited by examiner

Primary Examiner—William E. Kamm
(74) Attorney, Agent, or Firm—Shoemaker and Mattare, Ltd.

(57) ABSTRACT

With a method and a device for producing a helper signal for determining the point in time for a defibrillation or a cardiac massage given a cardiac arrest, the value (W) of the blood flow (B) into the head of the patient affected by the heart malfunctioning is used in order on the one hand to determine the necessity for activating the reanimation impulse (current shock/cardiac massage) and in order on the other hand to indicate whether the blood supply of the brain is sufficient.

Figure 1:
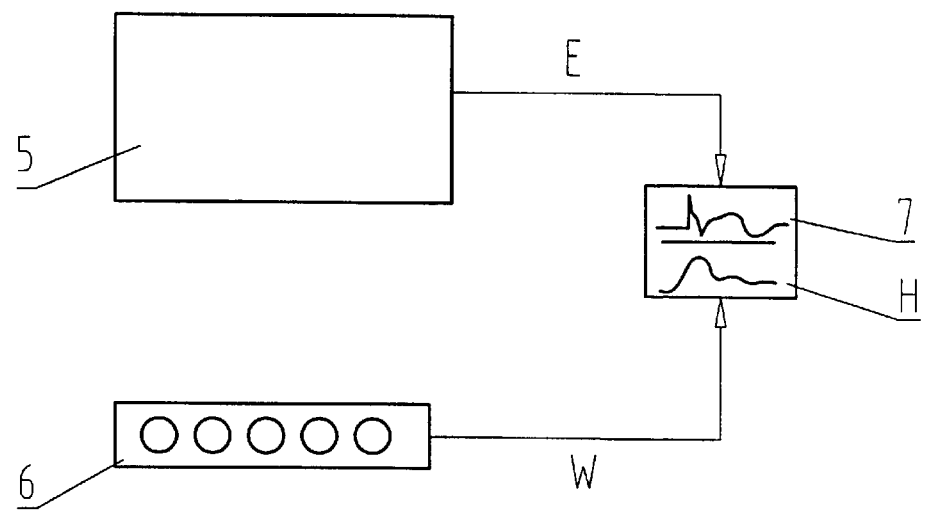

In order to be able to quickly lay the arrangement for measuring the blood flow onto the carotid artery, the measuring arrangement (10) consists of a multidude of individual flow measuring units (11, 11') arranged next to one another.

16 Claims, 7 Drawing Sheets

METHOD AND DEVICE FOR PRODUCING A HELPER SIGNAL

The invention relates to a method and a device for producing a helper signal with the features of the preamble of the independent patent claims. Furthermore the invention relates to a flow measuring arrangement which is particularly suitable for the method according to the invention and the device according to the invention.

It is known with a cardiac arrest or with heart malfunctioning to apply electroshocks or cardiac massage. Defibrillators (for producing electroshocks) or cardiac massages are often used in first aid activity. Electrical stimulations may however also be carried out via external pacemakers.

It is important to know at which point in time and whether a defibrillation or a cardiac massage must be carried out. With a tachycardia or rhythm malfunctioning defibrillations may also be carried out when a pulse is ascertained, but is irregular or too fast. Generally, a defibrillation should only be carried out, when with the patient a pulse can no longer be ascertained. Normally with this the (carotid) pulse of the patient is manually felt. With this above all with a weak pulse a superposition of the pulse of the patient with the pulse of the helper may arise.

Furthermore it is important to determine the necessity of a defibrillation or of a cardiac massage as well as the point in time at which the reanimation may be stopped.

It is further known to check the course of a reanimation with an electrocardiogram.

Such a checking of the reanimation however has various disadvantages. The blood circulation of the head must be recreated within three minutes of cardiac arrest in order to avoid irreparable brain damage. Although during a reanimation a heart beat may already set in and lead to a corresponding ECG signal, however the blood circulation of the brain is not yet sufficient to permit the halt of the reanimation.

On account of the ECG signal alone it is furthermore difficult to determine the necessity for activating the defibrillation current or cardiac massage. For this reason during the reanimation the pulse of the patient is manually measured. A defibrillation is not only activated with a loss of pulse.

Defibrillation may be required in varying situations. With so-called ventricular fibrillation (i.e. with irregular electrical action potentials with a frequency band width of 0 to approx. 15 Hz) the fibrillation may be ended by defibrillation. After the defibrillation has been effected the heart again finds its own rhythm. The pump output with ventricular fibrillation is practically equal to zero.

With so-called tachycardia the pulse beat with a heart which is not strained is very high. The beat volume with this is considerably reduced. Tachycardia may lead to ventricular palpitation which in turn leads to ventricular fibrillation.

In both cases a defibrillation is only carried out as soon as a pulse can no longer be felt. As soon as the pulse can be felt, synchronously a defibrillation with a low energy step (cardioversion) may be carried out.

With ventricular fibrillation the delivery of shock is effected a synchronously to the ECG, with cardioversion the delivery of shock is effected synchronously to the R-zag of the ECG.

With all applications of defibrillation the mechanical activity of the heart is acquired. Since often in the extremities of the patient a hypoxaemia prevails, the carotid pulse at the carotid artery is measured.

Above all with cardiac pressure massage the mechanical condition of the heart is important. The pressure point and the massage frequency should be determined in dependence on the measured pumping volume and where appropriate be changed, i.e. optimised.

It is the object of the present invention to avoid the disadvantages of that which is known, thus in particular to provide a method and a device for producing a helper signal as an aid to the decision for the activation of a defibrillation and/or a cardiac massage with heart malfunctioning, which ensures that the reanimation is only ended after reaching an adequate circulation of the brain. Furthermore the necessity to activate the individual defibrillation current shocks or cardiac massage is to be able to be determined with the method according to the invention and with the device according to the invention.

According to the invention these objects are achieved with a method and a device with the features of the characterising part of the independent patent claims.

In a method for producing a helper signal for determining the point in time for the actuation of a defibrillation and/or a cardiac massage with heart malfunctioning of a mammal, in particular of a human, the flow or the speed of the blood in the carotid artery is measured and a helper signal is activated dependent on the value of the speed of the blood flow into the head of the mammal and where appropriate dependent on an ECG signal. With this the basic concept of the invention lies in the fact that the pulse, in particular the blood flow into the head is automatically measured and displayed in the form of a helper signal. The helper signal may be used for determining the necessity of a treatment, for optimising the treatment or for monitoring. The helper signal aids the treating person.

In this context heart malfunctioning is to be understood as a momentary cardiac arrest as well as also an insufficient or irregular heart beat. Here and in the following a heart beat is to be understood as the contraction of the cardiac muscle.

The activation of electroshocks for the reanimation of the heart (defibrillation) and the drawing up of electrocardiograms during the reanimation is already known as such and is not the subject-matter of the present invention.

Principally the method according to the invention may be used with a defibrillation as well as with a cardiac massage.

Because the helper signal is actuated in dependence on the value of the blood flow it is guaranteed that the reanimation is continued for so long until an adequate blood circulation of the brain is ensured. In combination with an ECG also the necessity of a defibrillation may be judged much better. Furthermore the dependence of the helper signal on the value of the blood flow leads to the fact that the helper signal may be produced synchronously with the heart beat. Above all with cardiac massage the helper signal permits a feedback. In dependence on the signal the pressure point for the massage may be optimised. The helper signal furthermore also lends itself to monitoring.

In this context blood flow is to be understood as the volume of blood which flows from the heart into the head part per certain unit of time. The flow of blood may be measured most simply at the carotid artery.

Thanks to the helper signal an ambulance man may follow the pulse in the carotid artery without having to manually measure. In a further developed embodiment example the value of the blood flow is compared to a predeterminable nominal value. As long as at least the value of the amplitude of the blood flow lies below the corresponding nominal value, the helper signal is actuated. As soon as a heart beat can be recognised the helper signal is preferably activated at the point in time of the heart beat (i.e. at maximum flow) as long as the value of the maximum flow lies below the nominal value. The comparison arrangement computes, proceeding from the signals, the necessity and where appropriate the point in time for carrying out a reanimation.

As soon as a heart beat sets in after cardiac arrest, the helper signal may be used for monitoring the efficiency of the heart activity.

As a helper signal basically any signal is conceivable which displays to the person doing the treating the blood flow or the heart beat for activating the defibrillation and/or the cardiac massage. Acoustic or optical signals can be particularly simply realised and are effective. As an optical signal for example a flow curve indicated on a monitor but also a signal lamp are conceivable.

The helper signal may continuously display the value of the flow as a time-dependent curve. It is however also conceivable to produce a signal on reaching the amplitude value.

Furthermore it would be conceivable to directly couple the helper signal to a device for defibrillation or to a device for cardiac massage and to automatically activate the current shock for the defibrillation or the cardiac massage, or to block the defibrillator as soon as an adequate blood flow is measured.

The device according to the invention for producing a helper signal consists essentially of an arrangement for the non-invasive measurement of the blood flow and of means coupled to this for producing a helper signal, and advantageously of an arrangement for producing an ECG signal known per se.

For measuring the blood flow principally any flow measuring arrangements may be used. A measuring cell based on the Doppler effect is particularly advantageous. Doppler measurements for determining the speed of the blood in blood vessels are already known for diagnostic purposes.

It is moreover also conceivable for producing the helper signal to apply other pulse measuring arrangements not based on a flow measurement.

Advantageously the means for producing a helper signal consist of an acoustic or optical signal emitter. It is however also conceivable to couple the helper signal as an electronic signal directly to a defibrillator or to an arrangement for carrying out a cardiac massage.

As an additional measure it is also conceivable to apply the electrode of the defibrillator for determining the mechanical heart activity. This electrode during the defibrillation is applied between the heart and the collarbone. With this the electrode lies near to the tip of the heart.

The detection of the heart activity may at the same time be effected via ultrasound. The advantage lies in the fact that gel for the defibrillation may be simultaneously used for the ultrasound measurement. The ultrasound sensor at the same time may be applied directly into an electrode.

The conducting gel is thus simultaneously used for the defibrillation and for the ultrasound measurement, which simplifies the application.

As a gel advantageously a self-adhesive gel is applied.

Since with a cardiac arrest the reanimation must be started as quickly as possible, no time must be lost in localising the carotid artery for placing on the arrangement for measuring the blood flow. According to a particularly advantageous embodiment example of the present invention the arrangement for non-invasive measurement of the blood flow consists of a multitude of flow measuring units arranged next to one another. The signal outputs of the individual flow measuring units are coupled to a signal processing arrangement. Thanks to this embodiment form the measuring arrangement according to the invention may be layed onto the neck of the patient without an exact application being necessary. Independently of how the arrangement is placed onto the neck of the patient, always one flow measuring unit is correctly positioned on the carotid artery.

Advantageously the measuring arrangement comprises about 3 to 10 measuring units arranged next to one another. Each measuring unit has a surface with approx. 4 mm diameter to 8 mm diameter. As measuring units preferably piezoelectric measuring cells based on the measurement of the Doppler effect are used. It is however also conceivable to arrange other known measuring units in the way and manner according to the invention.

Advantageously a row of transducer elements lying next to one another are used. Transducers functioning in the pulsed wave as well as in the continuous wave method may be applied.

Alternatively it is conceivable to provide two rows of transducers arranged displaced to one another. As a result the probability that in each case a transducer comes to lie on the carotid artery may be increased to almost 100%.

Figure 2:
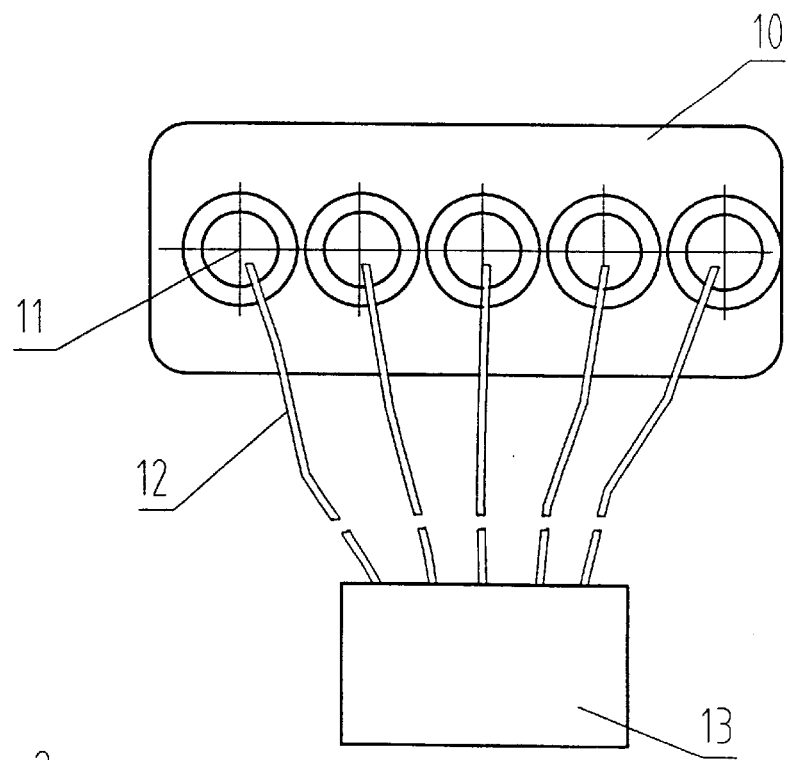
Figure 3:
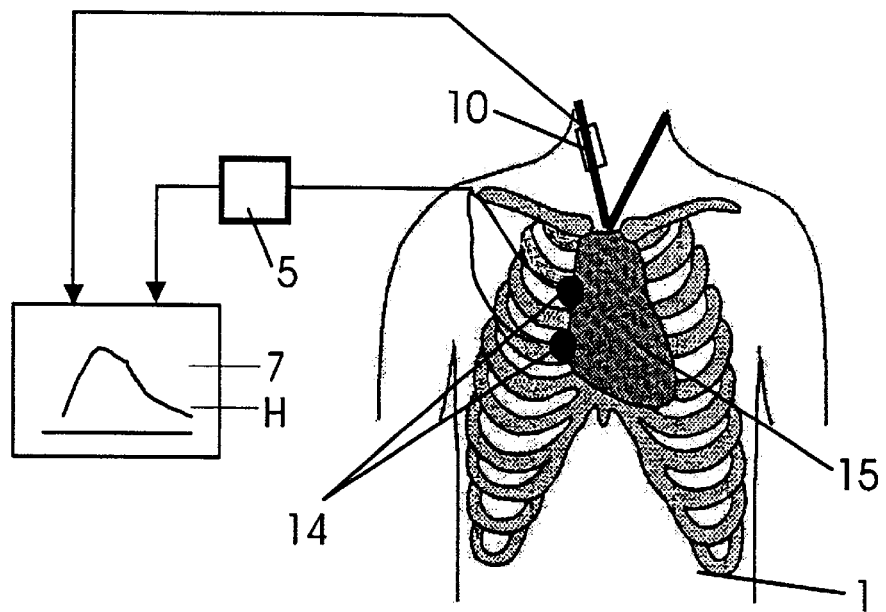
Figure 4:
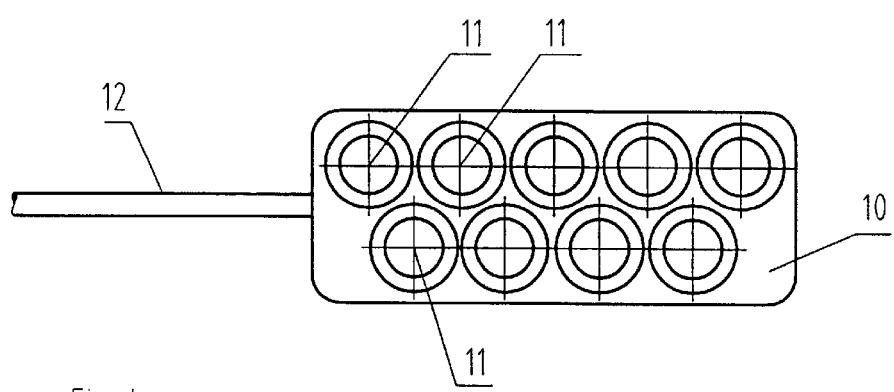

In the following the invention is described in more detail in embodiment examples and by way of the drawings. There are shown:

FIG. 1 a schematic representation of a device for producing a helper signal, according to the invention, FIG. 2 a schematic representation of a measuring arrangement according to the invention, FIG. 3 a schematic representation of a device according to the invention in use on a human body, FIG. 4 an alternative embodiment example of a measuring arrangement, and FIGS. 5a to 5e sketches of the course of the various embodiment examples according to the invention.

In FIG. 1 there is shown a device 3 according to the invention, for producing a helper signal H. The device 3 consists essentially of a first arrangement 5 for producing an ECG signal E and of a second arrangement 6 for the noninvasive measurement of the value W of a blood flow B. The arrangements 5, 6 are coupled to the means 7 for producing helper signals H.

The means 7 show an ECG curve and the value of the measured blood flow in dependence on the time.

FIG. 2 shows schematically a measuring arrangement 10 according to the invention for non-invasive measurement of the blood flow. The measuring arrangement 10 consists of five flow measuring units 11 arranged next to one another. The outputs 12 of the flow measuring units 11 are coupled to a signal processing arrangement 13. The signal processing 13 may be integrated in the comparison arrangement 8 (see FIG. 1). The flow measuring units 11 have a diameter of 4 to 5 mm. Measuring units based on the principle of the Doppler effect measurement are used in the pulsed or in the continuous wave method. According to the purpose of application the frequency range of the transducer varies. For measuring the carotid pulse a frequency of 8 MHz is used. For determining the pulse on deeper lying arteries frequencies of 4 to 2 MHz may be used.

According to the present embodiment example the outputs 11 of the flow measuring units are connected to the digital-signal processor.

If the measuring arrangement 10 according to the invention is layed onto the neck of a patient, always one of the flow measuring units 11 lies on or neighbouring the carotid artery. This flow measuring unit 11 produces a signal which represents the value of the blood flow. The remaining flow measuring units which do not lie directly neighbouring the carotid artery produce a weaker or no signal.

Of course it is also conceivable with a signal processing arrangement 13 to take into account the readings of all flow measuring units 11 and to compute an integrated signal. This may above all be advantageous with arrangements with which the dimensions of the flow measuring units 11 are selected such that more than one flow measuring unit simultaneously lies neighboring the carotid artery.

In FIG. 3 there is schematically shown a human body 11 and the device 3 according to the invention. Electrodes 14 are positioned on the body 1 for producing an electrocardiogram. An ECG arrangement 5 produces an ECG signal E. Simultaneously a second arrangement 6 for measuring the blood flow with a measuring arrangement 10 is laid onto the neck part of the body 1. The measuring arrangement 10 produces a signal which corresponds to the speed of the blood and thus is proportional to the value W of the blood flow B.

On account of the helper signal H it may be decided whether a defibrillation shock or a cardiac massage should be carried out and how long the reanimation must be continued. The reanimation should be carried out for so long until the blood flow is physiologically sufficient for the supply of the brain.

In the schematic representations the helper signal H is represented as an optical output on a monitor. Of course any of the other previously described helper signals are conceivable.

In FIG. 4 an alternative embodiment example of a measuring arrangement 10' is shown. The individual flow measuring units 11' are arranged in two rows displaced to one another. With this the resolution can be increased, or the probability of a flow measuring unit in each case lying exactly on the carotid artery may be increased.

The individual flow measuring units 11, 11' may be cast in silicon rubber or also rigidly connected to one another.

Figure 5A:
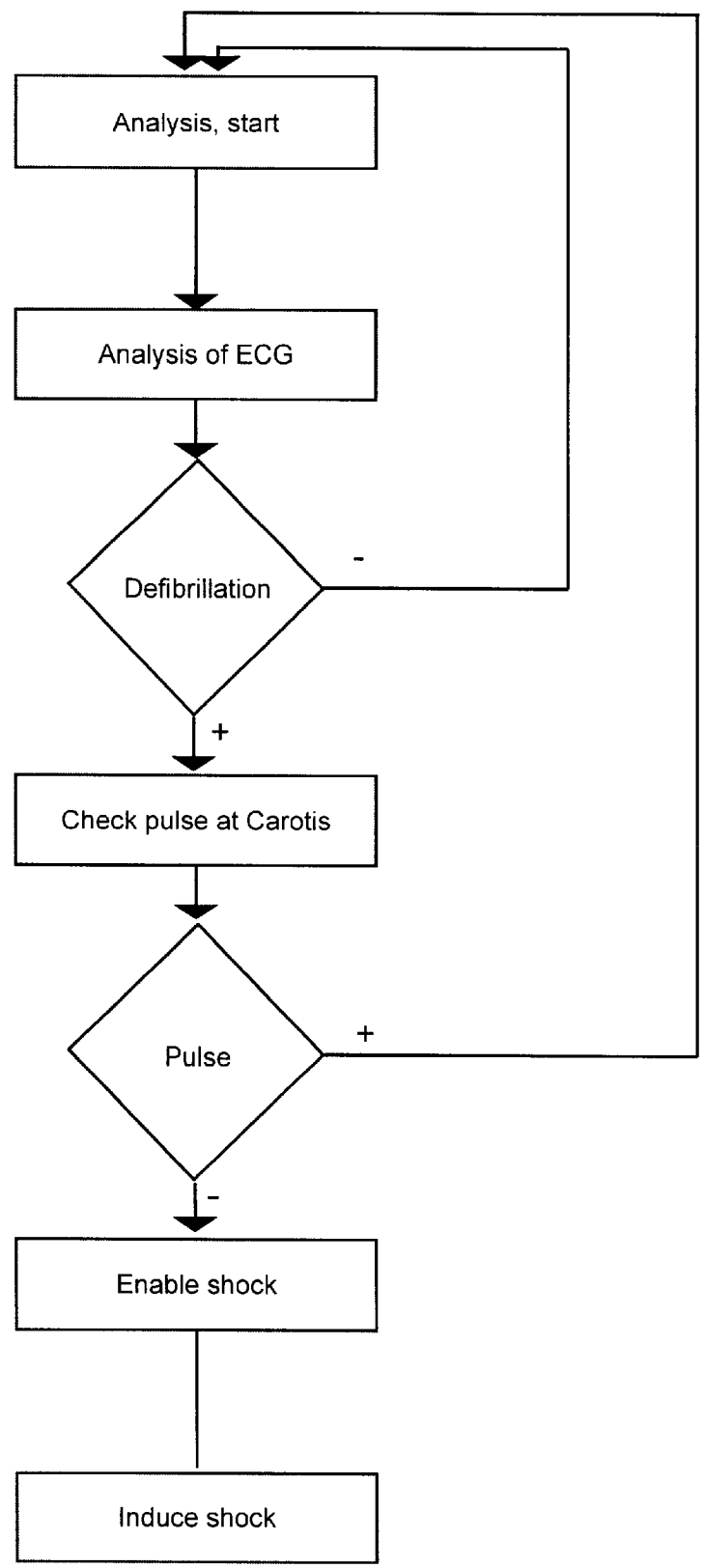

In FIG. 5a schematically the course of a first embodiment example for the semi-automatic defibrillation is shown. Before a defibrillation is carried out an analysis cycle is carried out by actuation of a start button. With this firstly a ECG analysis is carried out. On account of the ECG analysis it is (automatically) decided whether a defibrillation is necessary. If no defibrillation is necessary, the analysis cycle is set back to the original condition.

If on account of the ECG analysis a defibrillation seems necessary, firstly the helper signal H according to the invention is produced, i.e. the pulse at the carotid is measured. If a pulse is present one may not defibrillate. If no pulse is present a defibrillator for actuating a shock is released. The actuation of the shock is then effected manually by the ambulance man.

Figure 5B:
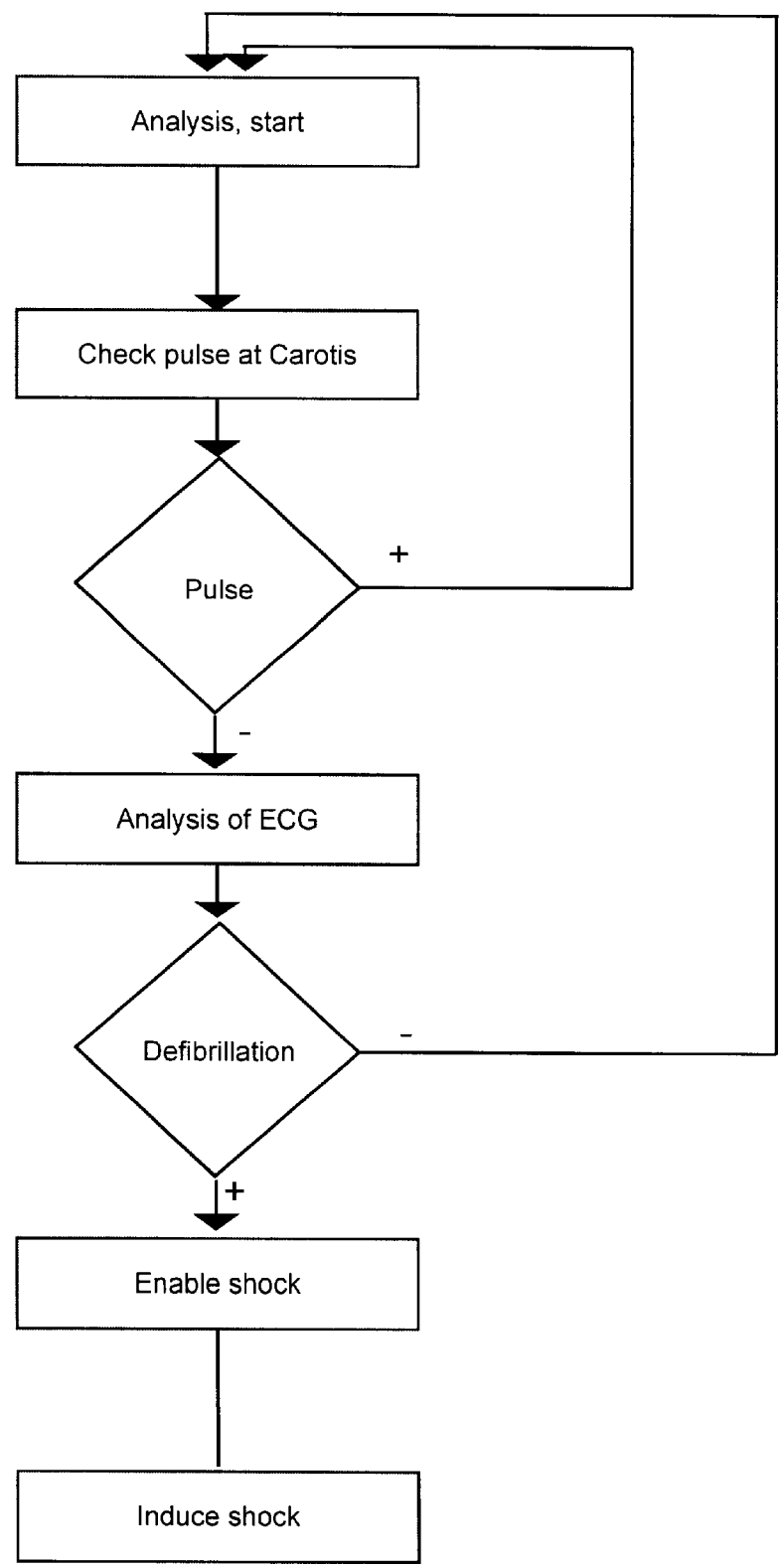

In FIG. 5b there is shown an alternative embodiment example of such an analysis cycle. With this firstly the carotid pulse is tested. If a pulse can be detected no defibrillation is required and the analysis cycle is set back into the original condition. With this embodiment example an ECG analysis is only carried out when an insufficient pulse or flow is measured.

The decision as to whether, proceeding from a measured pulse, one should defibrillate is effected by comparison of the pulse frequency or the blood flow with nominal values. The measured speed profile of the blood, where appropriate in combination with the pulse frequency may furthermore be applied for supressing malfunctioning, for example movement artifacts.

Figure 5C:
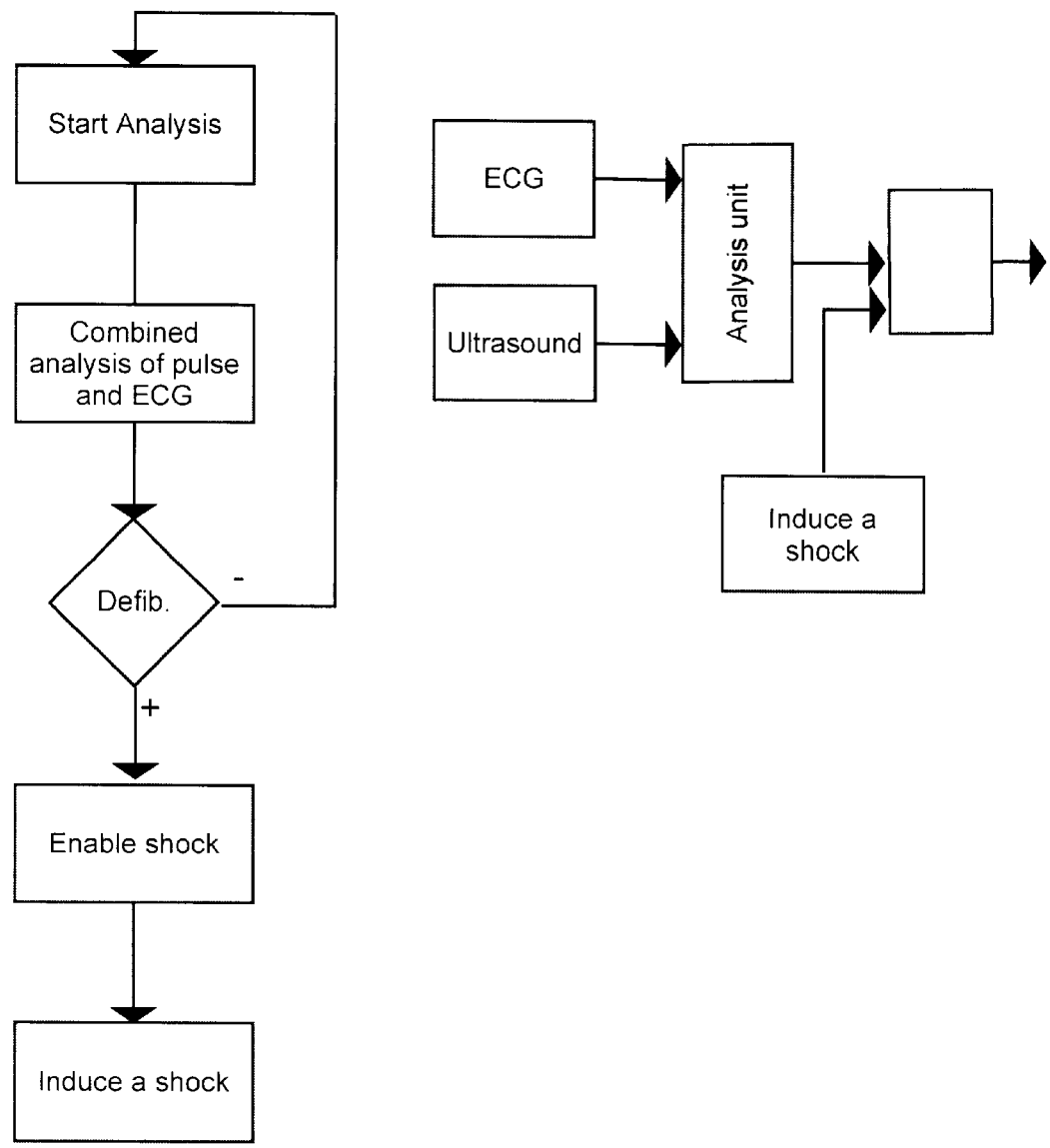

In FIG. 5c there is shown an embodiment example of an analysis cycle with which the helper signal representing the blood flow is simultaneously fed with an ECG signal into an analysis unit. The combined analysis of ECG and the pulse permits the verification of the evaluated results. Since ECG and pulse are in relation to one another with respect to time, the combined analysis permits the elimination of measurement errors.

Otherwise the embodiment example according to FIG. 5c functions similarly to FIGS. 5a and 5b. A defibrillation shock is only activated when the ECG is considered as warranting defibrillation and the flow measurement indicates an insufficient flow of blood.

Figure 5D:
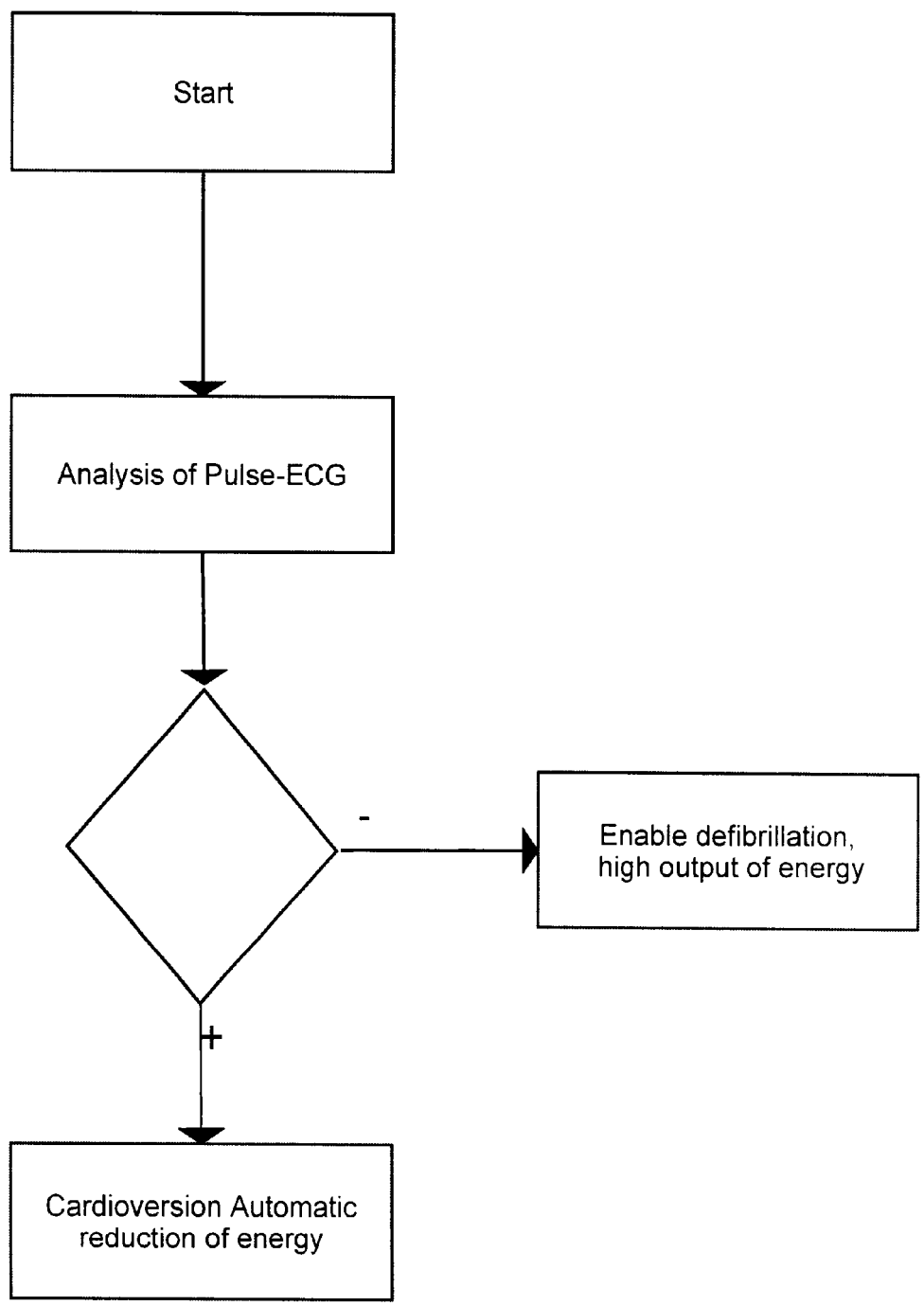

In FIG. 5d there is shown an embodiment example which automatically differentiates between a regular defibrillation and defibrillation with a cardioversion.

On account of the analysis of the pulse and ECG it is decided whether a conventional defibrillation is necessary. In this case a defibrillation current shock with a high energy is emitted.

In the case of a cardioversion (for example recognisable by too high a pulse frequency) automatically the energy of the defibrillation current shock is reduced.

Figure 5E:
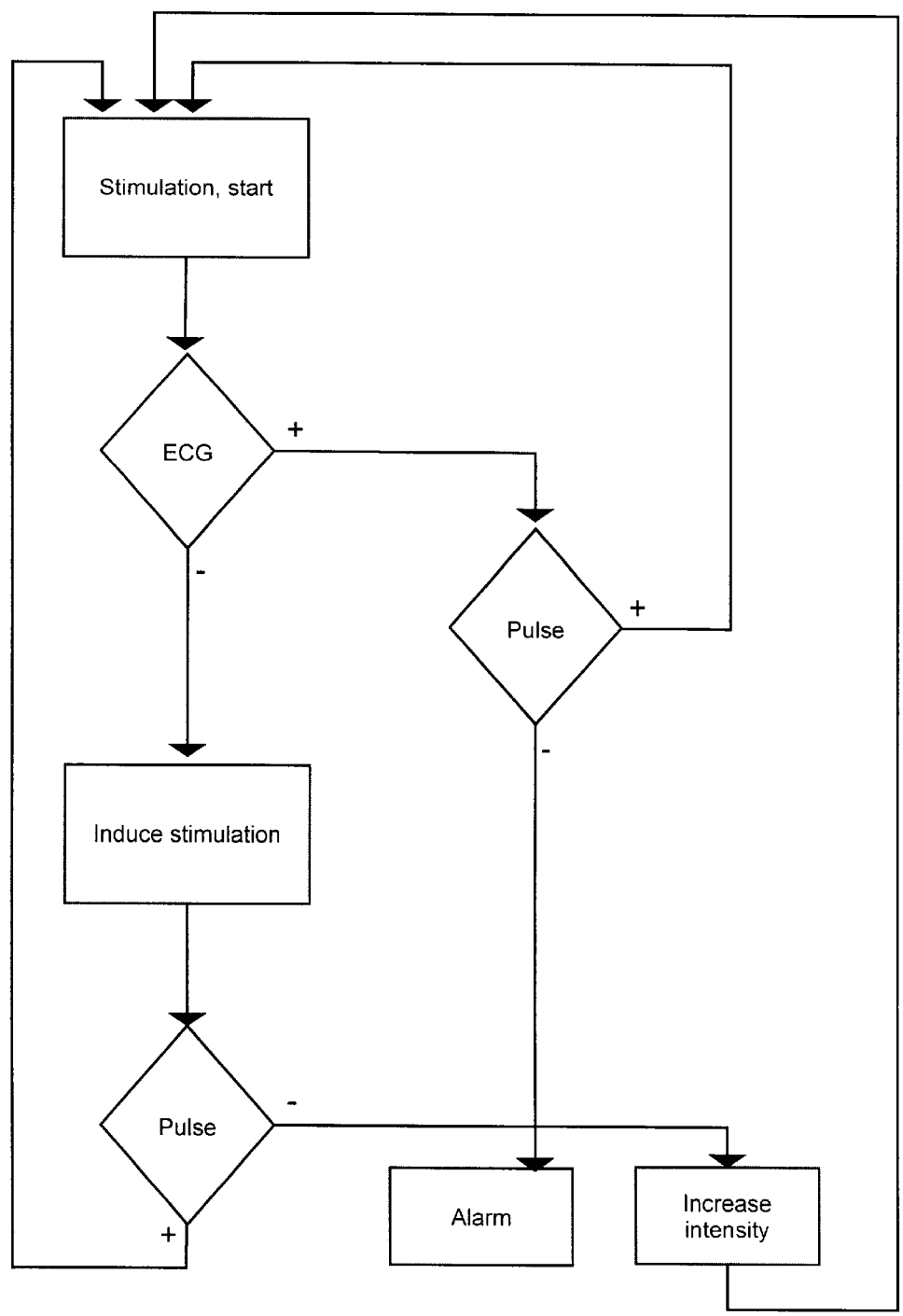

In FIG. 5e finally schematically an analysis cycle is shown with which the helper signal according to the invention is applied for monitoring and controlling a temporary external heart pacemaker.

With the presence of a sufficient ECG signal the helper signal is tested and it is decided whether a sufficient pulse prevails. If this is not the case an alarm is triggered.

If no sufficient ECG signal is determined an external stimulation is activated. Subsequently by way of the helper signal the pulse is measured. If after the stimulation still no pulse can be recognised, either an alarm is triggered or where appropriate a stimulation with an increased intensity is carried out.

In the various analysis cylces according to FIGS. 5a to 5e the helper signal is used in order to automatically determine and check the carotid artery pulse.

What is claimed is:

1. A method for determining the necessity and/or the timing of a treatment against heart malfunctions of a mammal, such as defibrillation or cardiac massage, said method comprising steps of applying an arrangement for the non-invasive measurement of the value of the flow of blood to the carotid artery of said mammal, determining the value of the flow of the blood into the head of said mammal with said arrangement, and producing a helper signal representing the value of the flow of blood into the head of said mammal.

2. A method according to claim 1, wherein the helper signal represents the time-dependent value of the blood blow.

3. A method according to claim 1, wherein the help signal is produced as an acoustic signal.

4. A method according to claim 1, wherein the help signal is produced as an optical signal.

5. A method according to claim 1, further comprising a step of coupling the helper signal to a defribrillator or to an arrangement for cardiac massage.

6. A device for determining the timing and/or the necessity of a treatment against heart malfunctions of a mammal, such as defibrillation or cardiac massage, said device comprising an arrangement for the non-invasive measurement of the flow of the blood, said arrangement being adapted to be placed onto the carotid artery of said mammal and means for producing a helper signal coupled to said arrangement for the non-invasive measurement of the flow of blood and responsive to the value of the flow of blood measured with said arrangement.

7. A device according to claim 6, wherein said means comprises an acoustic signal transmitter.

8. A device according to claim 6, wherein said means comprises an optical signal transmitter.

9. A device according to claim 6, further comprising means for coupling said helper signal to a defibrillator or to an arrangement for carrying out cardiac massage.

10. A device according to claim 6, wherein the arrangement for the noninvasive measurement of the flow of blood has a plurality of flow measuring units arranged in parallel.

11. A device according to claim 10, wherein the number of said flow measuring units is in the range of 4 to 10.

12. A device according to claim 10, wherein each flow measuring unit has a diameter of 0.5 to 1.0 cm.

13. A device according to claim 10, wherein the flow measuring units are Doppler effect measuring units having in a continuous wave mode.

14. A device according to claim 10, wherein the flow measuring units are Doppler effect measuring units having in a pulsed mode.

15. A device according to claim 10, wherein the flow measuring units are arranged in a single row.

16. A device according to claim 10, wherein the flow measuring units are arranged in two rows.

* * * * *